United States Patent
Khac et al.

(10) Patent No.: US 10,803,721 B2
(45) Date of Patent: Oct. 13, 2020

(54) METHOD FOR SUPPORTING A USER AND USER DEVICE

(71) Applicant: Sony Corporation, Tokyo (JP)

(72) Inventors: Tri Vu Khac, Stuttgart (DE); Gert Ceulemans, Stuttgart (DE); Francis Meyvis, Stuttgart (DE); Hugo Embrechts, Stuttgart (DE); Igor Bondarenko, Stuttgart (DE)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/358,727

(22) Filed: Mar. 20, 2019

(65) Prior Publication Data

US 2019/0295398 A1    Sep. 26, 2019

(30) Foreign Application Priority Data

Mar. 26, 2018 (EP) .................................... 18164053

(51) Int. Cl.
*G08B 21/04* (2006.01)
*G06F 3/01* (2006.01)
(Continued)

(52) U.S. Cl.
CPC ........ *G08B 21/043* (2013.01); *A61B 5/02055* (2013.01); *A61B 5/02438* (2013.01); *A61B 5/1112* (2013.01); *A61B 5/1117* (2013.01); *A61B 5/746* (2013.01); *A61B 5/747* (2013.01); *G06F 3/015* (2013.01); *G06F 3/017* (2013.01); *G08B 5/223* (2013.01); *G08B 21/0446* (2013.01); *G08B 21/0453* (2013.01); *G08B 21/182* (2013.01); *H04M 3/5116* (2013.01);
(Continued)

(58) Field of Classification Search
CPC .. G08B 21/043; G08B 5/223; G08B 21/0446; G08B 21/0453; G08B 21/182; A61B 5/02055; A61B 5/02438; A61B 5/1112; A61B 5/1117; A61B 5/747; G06F 3/015; G06F 3/017
USPC ...................................................... 340/573.1
See application file for complete search history.

(56) References Cited

U.S. PATENT DOCUMENTS 8,253,589 B2    8/2012 Grimm et al.
9,159,236 B2    10/2015 Lord et al.
(Continued)

FOREIGN PATENT DOCUMENTS

CN    104799826 A    7/2015
CN    104799826    *    6/2016
(Continued)

OTHER PUBLICATIONS

Extended Search Report issued in European Application 19159879.6-1115 dated Jun. 27, 2019.
(Continued)

*Primary Examiner* — Omar Casillashernandez
(74) *Attorney, Agent, or Firm* — Xsensus LLP (57) ABSTRACT

The present disclosure proposes a method for supporting a user. The method contains providing an acceleration measurement of the user and measuring at least one vital parameter of the user if the acceleration measurement is above a predefined acceleration threshold. A need of assistance for the user is signaled if the measured vital parameter of the user deviates from a standard vital parameter of the user by more than a predefined threshold.

17 Claims, 2 Drawing Sheets

(51) Int. Cl.

| | |
|---|---|
| *G08B 5/22* | (2006.01) |
| *G08B 21/18* | (2006.01) |
| *A61B 5/00* | (2006.01) |
| *A61B 5/0205* | (2006.01) |
| *A61B 5/11* | (2006.01) |
| *A61B 5/024* | (2006.01) |
| *H04M 3/51* | (2006.01) |
| *G08B 27/00* | (2006.01) |

(52) U.S. Cl.
CPC ............ *A61B 5/0022* (2013.01); *A61B 5/112* (2013.01); *A61B 5/681* (2013.01); *A61B 5/6898* (2013.01); *A61B 5/742* (2013.01); *A61B 5/7405* (2013.01); *G08B 27/005* (2013.01); *G08B 27/006* (2013.01)

(56) References Cited

U.S. PATENT DOCUMENTS

| | | | |
|---|---|---|---|
| 9,505,412 | B2 | 11/2016 | Bai et al. |
| 10,575,747 | B2 * | 3/2020 | Lau ...................... A61B 5/0448 |
| 2011/0199216 | A1 | 8/2011 | Maria et al. |
| 2015/0126909 | A1 | 5/2015 | Hogrel et al. |
| 2016/0029966 | A1 * | 2/2016 | Salas-Boni ........ A61B 5/14532 600/347 |
| 2016/0035206 | A1 | 2/2016 | Pai et al. |
| 2018/0110434 | A1 * | 4/2018 | Lau ...................... A61B 5/7235 |
| 2019/0125241 | A1 * | 5/2019 | Patek .................. A61B 5/0022 |
| 2019/0295398 | A1 * | 9/2019 | Khac .................. G08B 21/0446 |
| 2019/0382025 | A1 * | 12/2019 | Mena Benito ........... A61B 5/01 |

FOREIGN PATENT DOCUMENTS

| | | |
|---|---|---|
| CN | 103377539 B | 8/2017 |
| EP | 2 587 240 A2 | 5/2013 |
| FR | 2887669 A3 | 12/2006 |
| KR | 10-1680598 B1 | 12/2016 |
| WO | 2012/146957 A1 | 11/2012 |
| WO | 2015/103127 A1 | 7/2015 |

OTHER PUBLICATIONS

Devpost, "Connected Intersections", available at <https://intersections.devpost.com/submissions/26533-tug>, 7 pages.

Wang et al., "WalkSafe: A pedestrian safety app for mobile phone users who walk and talk while crossing roads", Hotmobile, Feb. 28-29, 2012, San Diego, CA, USA, 7 pages.

Sant, "Why drivers in china intentionally kill the pedestrians they hit", Sep. 4, 2015, 3 pages.

Office Action dated May 19, 2020 in European Patent Application No. 19 159 879.6, 6 pages.

* cited by examiner

METHOD FOR SUPPORTING A USER AND USER DEVICE

CROSS-REFERENCE TO RELATED APPLICATION

The present application claims priority to European Patent Application 18164053.3 filed by the European Patent Office on Mar. 26, 2018, the entire contents of which being incorporated herein by reference.

FIELD

The present disclosure provides concepts for supporting a user. A method for supporting a user is proposed. Further embodiments relate to a user device.

BACKGROUND

In some situations a person needs support or assistance, e.g. when the person is in a hazardous situation or has had an accident. However, there might not always be someone present to support the person or e.g. to call for an emergency service, if necessary. Sometimes it is important to provide assistance to the person as soon as possible.

A person could get in distress on an empty road, e.g. in a quiet neighborhood of a city or at times when few people are on the streets like in the early morning or late at night. A person could also get in distress in remote areas like a forest or in the mountains, e.g. during leisure activities. The person, e.g. a pedestrian or a cyclist, may be in distress after an accident, for example having tumbled or fallen from his bike.

The person in distress might call for help by using a mobile phone to inform someone about his situation. In some circumstances though, it may be impossible for the person to use his mobile phone and he might be unable to call for assistance.

There is a need for improving concepts for providing support to a person.

SUMMARY

This need is met by methods and devices in accordance with the independent claims. Advantageous embodiments are addressed by the dependent claims.

An embodiment of the disclosure relates to a method for supporting a user. According to the method, an acceleration measurement of the user is provided. The method comprises measuring at least one vital parameter of the user if the acceleration measurement is above a predefined acceleration threshold. Further, a need of assistance for the user is signaled if the measured vital parameter of the user deviates from a standard vital parameter of the user by more than a predefined threshold.

Another embodiment relates to a user device. The user device comprises circuitry configured to provide an acceleration measurement of the user and to initiate a measurement of at least one vital parameter of the user if the acceleration measurement is above a predefined acceleration threshold. Further, the circuitry is configured to signal a need of assistance for the user, if the measured vital parameter of the user deviates from a standard vital parameter of the user by more than a predefined threshold.

BRIEF DESCRIPTION OF THE FIGURES

Some examples of apparatuses and/or methods will be described in the following by way of example only, and with reference to the accompanying figures, in which.

DETAILED DESCRIPTION

Various examples will now be described more fully with reference to the accompanying drawings in which some examples are illustrated. In the figures, the thicknesses of lines, layers and/or regions may be exaggerated for clarity.

Accordingly, while further examples are capable of various modifications and alternative forms, some particular examples thereof are shown in the figures and will subsequently be described in detail. However, this detailed description does not limit further examples to the particular forms described. Further examples may cover all modifications, equivalents, and alternatives falling within the scope of the disclosure. Same or like numbers refer to like or similar elements throughout the description of the figures, which may be implemented identically or in modified form when compared to one another while providing for the same or a similar functionality.

It will be understood that when an element is referred to as being "connected" or "coupled" to another element, the elements may be directly connected or coupled or via one or more intervening elements. If two elements A and B are combined using an "or", this is to be understood to disclose all possible combinations, i.e. only A, only B as well as A and B, if not explicitly or implicitly defined otherwise. An alternative wording for the same combinations is "at least one of A and B" or "A and/or B". The same applies, mutatis mutandis, for combinations of more than two Elements.

The terminology used herein for the purpose of describing particular examples is not intended to be limiting for further examples. Whenever a singular form such as "a," "an" and "the" is used and using only a single element is neither explicitly or implicitly defined as being mandatory, further examples may also use plural elements to implement the same functionality. Likewise, when a functionality is subsequently described as being implemented using multiple elements, further examples may implement the same functionality using a single element or processing entity. It will be further understood that the terms "comprises," "comprising," "includes" and/or "including," when used, specify the presence of the stated features, integers, steps, operations, processes, acts, elements and/or components, but do not preclude the presence or addition of one or more other features, integers, steps, operations, processes, acts, elements, components and/or any group thereof.

Unless otherwise defined, all terms (including technical and scientific terms) are used herein in their ordinary meaning of the art to which the examples belong.

Figure 1:
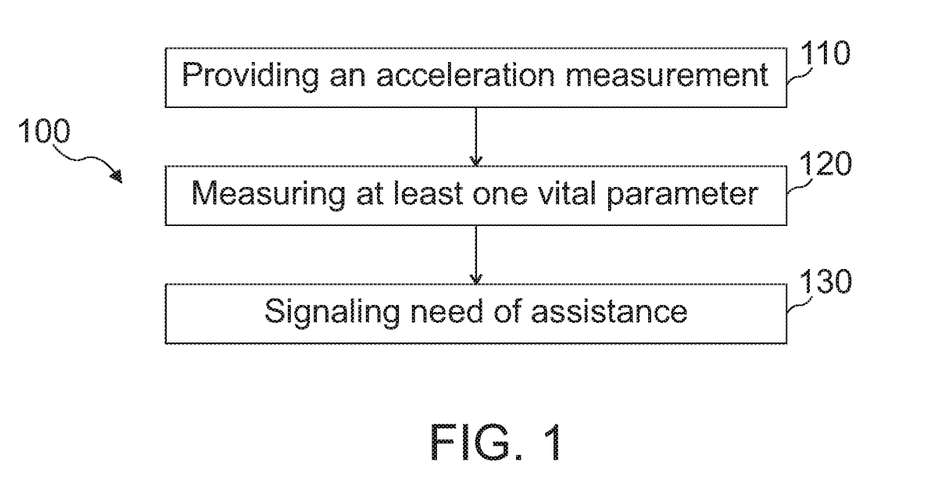
FIG. 1 shows an embodiment of a method for supporting a user.

FIG. 1 shows an embodiment of a method 100 for supporting a user. According to the method 100 an acceleration measurement of the user is provided 110. The method 100 comprises measuring 120 at least one vital parameter of the user if the acceleration measurement is above a predefined acceleration threshold. Further, a need of assistance for the user is signaled 130 if the measured vital parameter of the user deviates from a standard vital parameter of the user by more than a predefined threshold.

The method 100 can be used to reliably detect if the user, for example a person like a pedestrian, a walker, a hiker, a skater, a cyclist etc., is getting in distress and has need of assistance. Therefore, the method 100 uses two conditions that can be sequentially verified to increase an accuracy of detecting whether the user needs support.

For the first condition, an acceleration measurement is used 110 for detecting an acceleration above the predefined acceleration threshold and consequently indicating an acceleration of the user which is higher than usual. For example, if the user falls he may experience a stronger acceleration than when he walks as usual. A strong acceleration may indicate that the user is getting in distress, for example in an accident. However, there may be situations in which the user falls but has no need for assistance. After having fallen, the user could get up on his own and continue walking without need of assistance. Therefore, if an acceleration above the predefined acceleration threshold is detected, in a second part of the method, a further measurement is performed, measuring 120 at least one vital parameter of the user. Using the vital parameter measurement can increase the reliability of detecting if the user really has need of assistance.

For the second condition, the measured vital parameter is compared with a corresponding standard vital parameter of the user. A user for example may fall or stumble without having need of assistance. In this case, the vital parameters of the user may remain constant, or normal, or may return to normal quickly, and an evaluation of the vital parameter may show that the user has no need of assistance so that no need of assistance is signaled after detecting the acceleration. By contrast, if the user is in trouble, because, for example, falling happened due to a stronger accident, the vital parameters of the user may change. After an accident, vital parameters like the heartbeat or the blood pressure of the person having the accident may change significantly. The change can be detected by comparing the measured vital parameters after the acceleration measurement with standard vital parameters of the user, enabling indicating e.g. an accident of the user.

The at least one standard vital parameter relates to vital parameters of the user present when the user is in a normal condition without having need of assistance. The standard vital parameter may be determined based on vital parameters of the user measured before the acceleration above the predefined acceleration threshold is detected, for example. The vital parameter for generating the standard vital parameter may be measured by a user device in situations in which the user uses the user device under normal circumstances when he has no need of assistance. For example, based on vital parameter measurements before the detected high acceleration, an average value can be determined. The average value may be based on at least two (or a plurality of) measurements of the vital parameter. The vital parameters used for generating the average value may be measured in time intervals of e.g. 10 seconds (or of 30 seconds, 1 min., 5 min. or 10 min.). For example, the need of assistance can be signaled 130 if the measured vital parameter deviates from the average value by more than 20% (or by more than 30%, by more than 40% or by more than 50%) due to increase or decrease of the vital parameter after the high acceleration. Standard vital parameters may be determined for two, three, or a plurality of vital parameters.

Alternatively, the standard vital parameter may be an acceptable lower and/or higher threshold value of the vital parameter. For example, the lower threshold value may be 50% (or 60%, 70%, or 85%) of the average value and the measured vital parameter deviates from the standard vital parameter by more than a predefined threshold if it is lower than the lower threshold value. For example, the higher threshold value may be 150% (or 140%, 130%, or 115%) of the average value and the measured vital parameter deviates from the standard vital parameter by more than a predefined threshold if it is higher than the higher threshold value. The need of assistance can be signaled 130 if the measured vital parameter exceeds a range of the standard vital parameter between the lower and the higher threshold value.

Signaling 130 need of assistance may comprise sending a text message, an audio signal, a visual signal or a speech message. A message or a signal may be sent via a radio link by an electrical device of the user, e.g. performing measurements of the vital parameter, or by a cloud service performing the method, e.g. receiving the measured vital parameter and having access to the standard vital parameter.

Optionally, the need of assistance is signaled 130 depending on a degree of deviation between the measured vital parameter and the standard vital parameter. For example, signaling 130 the need of assistance may comprise sending an assistance requirement message to at least one of an emergency service, and a private "in case of emergency" contact. In an embodiment of the method 100, a first, lower deviation from the standard vital parameter (e.g. at least +/−20% and at most +/−50% from the average value) may cause to contact the private "in case of emergency" contact. By contrast, a second deviation, higher than the first deviation (e.g. more than +/−50% from the average value) may cause to contact the emergency service. Signaling 130 the need of assistance to an emergency service only in cases with high deviation of the measured vital parameter may decrease a risk of false alarms sent to the emergency service. For example, false alarms sent to a private "in case of emergency" contact may have less severe impacts and may be rather acceptable. For example, the assistance requirement message is sent to an emergency service if the deviation between the measured vital parameter and the standard vital parameter is over a predefined threshold, e.g. more than 100% of the standard vital parameter. A deviation of the vital parameter from the standard vital parameter by more than 100% may reliably indicate that the user is in distress and a risk of false alarms may be low. In one example, the mobile device may display an inquiry message "Should assistance be contacted?" In an example, the mobile device may be alerting the user by vibrations and/or sounds, and only contact assistance if the user does not react to the alert.

The standard vital parameter may depend on the type of the vital parameter. The vital parameter may comprise at least one of a heartbeat of the user, blood pressure of the user, skin response of the user, blood oxygen level of the user and skin temperature of the user, wherein a wearable device of the user is used for measuring the vital parameter. An acceptable deviation indicating that the user is in a normal condition may depend on the used vital parameter, as for a first vital parameter another deviation may be acceptable than for a second vital parameter. For example, when using the skin temperature of the user for deciding whether to signal 130 the need of assistance, the acceptable deviation may be lower than when using the heartbeat, for example. For example, the wearable device is at least one of a smartwatch, a heartbeat sensor, a smart bracelet, and a smart garment, configured to measure the vital parameter of the user. The wearable device may further comprise an acceleration sensor, configured to detect an acceleration above the predefined acceleration threshold in order to trigger the measurement of the at least one vital parameter after detecting the acceleration.

For example, for determining about the signaling 130 need of assistance two, or further vital parameters can be used simultaneously. By using a plurality of vital parameters for determining whether the user is in distress or not, a reliability of the determined state of the user may be increased. For example, if more than two vital parameters deviate from the respective standard vital parameters, the probability that the user is in distress can be high and an emergency service may be contacted at reduced risk of false alarms.

Optionally, in addition to measuring the vital parameter, a position of the user (e.g. a body position) is determined according to an embodiment and signaling 130 the need of assistance depends on the determined position of the user. For example, a body sensor of the user can determine whether the user is standing or lying. For example, if the user was standing before detecting the acceleration above the predefined acceleration threshold and the user is lying after the detected acceleration, this can indicate that the user is in distress. For example if the user gets up within a predefined time period, for example within 10 seconds (or within 20 seconds or within 30 seconds) no need of assistance might be signaled. By contrast, if after the predefined time period the user remains lying, the position may be used as indicator that the user is in distress (e.g. cannot get up on his own anymore), and the need of assistance may be signaled 130.

Optionally, a gait of the user is determined by an electrical device of the user as the vital parameter (additionally or alternatively to other vital parameters). A gait may be determined by an acceleration sensor (for example the same acceleration sensor used for detecting the acceleration above the predefined acceleration threshold) by determining periodical accelerations caused by the gait of the user. For example, the acceleration sensor is comprised by a device of the user that the user is carrying e.g. in his pocket. If the user walks, runs or cycles, the device experiences corresponding periodic accelerations usable for determining the gait, e.g. based on a strength and/or frequency of the accelerations. If after detecting the acceleration above the predefined acceleration threshold the gait remains constant, there may be no need for signaling the need of assistance for the user. By contrast, if the gait changes, for example a frequency of accelerations is lower (for example lower than 20% (or than 40%) compared to the frequency of the gait before the detected acceleration), a need of assistance may be signaled 130. For example, need of assistance may be signaled 130 if the user does not continue moving after the detected acceleration (e.g. no accelerations are detected or the walking has stopped). For example, an irregular gait may indicate that the user is in distress, as he is limping after an accident, for example.

For example, the standard vital parameter of the user is an averaged vital parameter of a plurality of vital parameters of the user measured within a predefined time range before the acceleration measurement above the predefined acceleration threshold was detected. For example, a user device of the user can continuously, for example with a frequency of one measurement per minute (or two or more measurements per minute), determine the recent vital parameter of the user. When detecting the acceleration, the recently determined vital parameters of the user (e.g. the average of the 10 last measured vital parameters or the vital parameters measured within a time range of 3 min. before detecting the acceleration) may be used as standard parameters of the user for the comparison. Using recent parameters of the user may enable an adaptation of the standard vital parameters corresponding to the recent situation or condition of the user.

Optionally, the standard vital parameter of the user can be determined based on a user profile determined during normal use of an electrical device used by the user. For example, every time the user uses the electrical device, it can determine a vital parameter of the user. Based on all determined vital parameters of the user profile, the standard vital parameter may be determined or generated. Using a standard vital parameter based on a user profile may enable comparison with the measured vital parameter after the detected acceleration with a general standard vital parameter of the user.

For example, the user may set an individual standard vital parameter. The user may set an individual value related to at least one vital parameter as the standard vital parameter and set an acceptable range around the standard vital parameter beyond that the measured vital parameter does deviate from the standard vital parameter. The user may set a lower and/or a higher threshold for acceptable vital parameters. The user may choose which vital parameters to use for determining a deviation. For example, the user could individually exclude a vital parameter that is regularly inconstant (for example, the blood pressure of the user may change significantly also under normal circumstances) and select a vital parameter that is regularly constant for being used to determine a potential deviation after detecting the acceleration.

Optionally, at least one vital parameter measured before detecting an acceleration above the predefined acceleration threshold can be transmitted to a cloud service and the standard vital parameter of the user can be determined by the cloud service based on at least one measured vital parameter. Alternatively, the standard vital parameter determined by a user device may be transmitted to the cloud service from the user device. For example, if the cloud service detects a deviation of the measured vital parameter from the standard vital parameter, the cloud service may signal 130 the need of assistance for the user. Signaling 130 the need of assistance for the user by the cloud service may increase the reliability of successfully signaling 130 the need of assistance as the cloud service may be constantly connected to a communication network, for example without a risk of no reception.

For example, signaling 130 the need for assistance comprises proposing to the user, by an electrical device of the user, to let the electrical device send an assistance requirement message, wherein in the absence of a user reaction the assistance requirement message is sent automatically by the electrical device with a predefined time lag after the proposal. For example, the electrical device may support the user by proposing sending a predefined assistance requirement message and the user only has to press a button to send it. This may avoid that the user has to text the assistance requirement message when being in distress or has to call the emergency service himself. For example, if the user does not react to the proposal within a time lag of 10 seconds (or within 20 seconds or within 30 seconds), the electrical device may automatically send the assistance requirement message as it may be probable that the user is unable to react and has need of assistance. The assistance requirement message may comprise at least information about the location of the user, indicated for example by the location of the electrical device itself. The electrical device may comprise a positioning sensor like a global positioning system GPS sensor to determine its recent position.

Optionally, the predefined acceleration threshold used to initiate measuring the vital parameter is adjusted by the user. For example, the user can adjust the acceleration threshold by giving a user input received by a device of the user and/or a cloud service providing performing the method for supporting a user. The user may adjust the predefined acceleration threshold according to a recent situation of the user, for example. A first user might be a calm walker and may require reducing the predefined acceleration threshold. A second user might be a sportive biker, experiencing usually higher accelerations due to his sportive biking style. The second user may increase the predefined acceleration threshold for avoiding regular detections of acceleration and performing measurements of vital parameters if not necessary.

Figure 2:
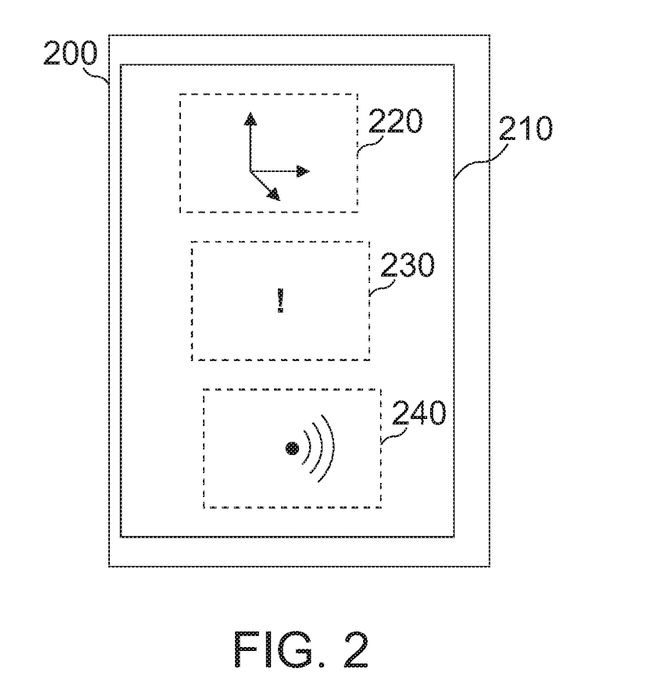
FIG. 2 shows a user device comprising circuitry.

FIG. 2 shows an embodiment of a user device 200. The user device 200 comprises circuitry 210 configured to provide an acceleration measurement of the user. The circuitry 210 is further configured to initiate a measurement of at least one vital parameter of the user if the acceleration measurement is above a predefined acceleration threshold, and is configured to signal a need of assistance for the user, if the measured vital parameter of the user deviates from a standard vital parameter of the user by more than a predefined threshold. The user device 200 may be a mobile device, a smart phone, a smart watch, a smart wearable etc.

According to an embodiment, the user device 200 or the circuitry 210 can comprise an acceleration sensor 220. The acceleration sensor 220 may be configured to provide or perform the acceleration measurement and detect accelerations above a predefined acceleration threshold. As a user may carry the user device 200 with him, an acceleration of the device measured by the acceleration sensor 220 may be used as acceleration measurement of the user. The acceleration sensor 220 may be an accelerometer, for example comprising piezoelectric, piezoresistive and/or capacitive components. The acceleration sensor 220 may be a micro electromechanical system (MEMS) acceleration sensor, e.g. an acceleration sensor comprising a proof mass or a thermal accelerometer, resulting in a small size and/or increased reliability of the sensor. Alternatively, the acceleration measurement can be based on an evaluation of a change of the position of the user device 200. For example, a fast change of position may indicate strong acceleration, for example above the predefined acceleration threshold. The respective positions may be determined based on a positioning system (for example global positioning system GPS) or based on a radio system configured to determine positions of the device (e.g. WLAN).

In an embodiment, the user device 200 or the circuitry 210 comprises a measurement initiation device 230. The measurement initiation device 230 can be configured to receive an information if the acceleration measurement is above the predefined acceleration threshold and can for example send a request to start measuring at least one vital parameter of the user. For example, the request can be sent to the acceleration sensor 224 measuring the gait of the user. Additionally or alternatively, the request can be sent to at least one body sensor connected to the user device 200 and configured to measure vital parameters of the user. For example, the circuitry 210 can be configured to receive a response from the body sensor comprising the measured vital parameter of the user. The user device 200 may comprise a receiver configured to receive information about the vital parameter measured and transmitted by a wearable device of the user connected to the user device, the wearable device for example comprising at least one body sensor.

In an embodiment, the user device 200 comprises at least one sensor configured to measure a vital parameter of the user using the user device 200. For example, the user device 200 may be a smartwatch (or may be comprised by a smartwatch) being able to measure blood pressure and/or heartbeat of the user. The circuitry 210 may initiate the measurement of the at least one vital parameter by requesting the at least one sensor of the user device 200 to perform the measurement.

For example, the user device 200 or the circuitry 210 may comprise a signaling device 240 configured to signal the need of assistance. The signaling device may be a radio transceiver configured to send a radio message (for example via a mobile network, like GSM, LTE, etc. and/or via a wireless connection, e.g. WLAN, Bluetooth, etc. for example via the Internet and/or directly to another electrical device) comprising information about the need of assistance for the user. In an embodiment, the user device comprises a transmitter, for example a radio transmitter, configured to send an assistance requirement message. Sending the radio message or the assistance requirement message may provide support or assistance to the user, for example if the user himself is in distress and unable to send such message.

According to an embodiment, the user device 200 is configured to output at least one of an acoustic signal and a light signal to signal the need of assistance for the user. For example, the user device 200 may comprise an acoustic speaker and the acoustic signal can be outputted by the acoustic speaker. For example, the acoustic signal can be an alarm signal, a siren alarm and/or a speech signal comprising information about the need of assistance for the user. Outputting the acoustic signal may support the user, for example if the user cannot call for help himself, for example in cases of physical shock after an accident. The acoustic signal may be outputted periodically and/or with increasing volume, to increase a probability that some other third person around the user device 200 may hear the acoustic signal and come to help the user. The user device 200 may output a light signal by activating a light source (e.g. a light emitting diode, LED) of the user device 200, e.g. with a predefined periodicity.

Optionally, the user device 200 is configured to adjust the predefined acceleration threshold according to a setting of a user (e.g. via a user input via a display of the user device 200). For example, if the user is a careful person, he could decrease the acceleration threshold compared to the predefined acceleration threshold of the user device 200. Alternatively, for example if the user is a sportive person, regularly exposed to higher accelerations (e.g. while trail running or mountain biking), the user could increase the acceleration threshold in order to prevent unnecessarily initiating measurements of the vital parameter of the user.

The user device 200 may in some situations support a person using the user device 200 by sending a message comprising information that the user has need of assistance. The user device 200 may propose to the user to call for help and/or automatically call for help, for example if the user device 200 determines that the user is in distress. The user device 200 may support the user by informing for example another person and/or an emergency service about the need of assistance or help for the user.

More details and aspects are mentioned in connection with the embodiments described above or below. The embodiments shown in FIG. 2 may comprise one or more optional additional features corresponding to one or more aspects mentioned in connection with the proposed concept or one or more embodiments described above or below (e.g. FIGS. 1 and 3).

Figure 3:
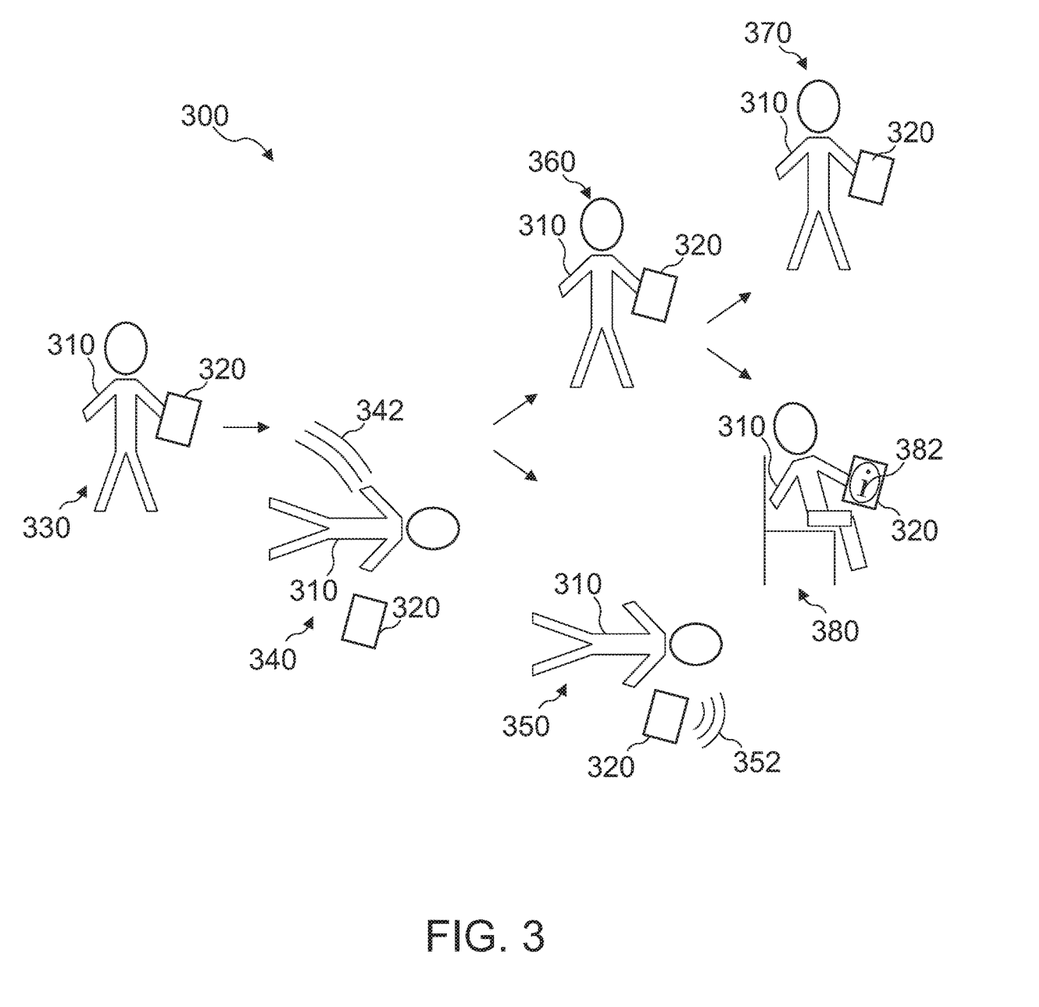
FIG. 3 shows an example of supporting a user with a user device.

FIG. 3 shows an example 300 of supporting a user 310 with a user device 320. The user 310 is for example a pedestrian carrying the user device 320 with him. The user device 320 comprises features according to features of the user device 200 presented above or below.

In a first situation 330, the user 310 may use the device 320 in normal condition. For example, the user may take a walk and the device may measure a plurality of vital parameters of the user (e.g. gait, heartbeat, blood pressure, etc.) for determining the standard vital parameter of the user. The standard vital parameter of the user may be stored on the user device 320. For example, biometric information of the user may be collected to determine the user's normal health state as standard vital parameter. This may allow to accurately distinguish between normal health conditions and distress situations, e.g. in case of an accident.

In a second situation 340 of the example 300, the user 310 falls, for example, he may stumble or have sudden health issues causing the falling. The user 310 may carry the device 320 with him (e.g. in his hand or in a pocket) so that when the user 310 falls also the user device 320 falls. Consequently, the user device 320 experiences an acceleration 342 that can for example be detected by an accelerometer of the user device 320. The acceleration 342 may be at least similar to the acceleration of the user 310 when falling so that it can be used as acceleration of the user to trigger measuring at least one vital parameter of the user. For example, the acceleration 342 is above the predefined acceleration threshold and a vital parameter of the user is measured by the user device 320 or the user device 320 initiates measuring the vital parameter. For example, when an accident happens to the user, a certain high energy acceleration will trigger the user device 320 (or a system with the user device 320) to check the vital parameters to determine the circumstances of the user. From the moment of acceleration above the acceleration threshold, the device may check whether: The user continues or resumes walking with the same or similar gait as before the trigger; The heartbeat and blood pressure stay within normal boundaries, as raising or falling by a significant amount could indicate a distress; Skin conductance changes (e.g., data from galvanic skin response sensors can be analyzed to detect event-related skin conductance responses to sensory stimuli); Skin temperature changes (e.g. drops); The user's movements changes (e.g. by using electromyography to determine the biomechanics of the user and to detect anomalies in the movement); Drops in blood oxygen levels occur, indicating issues with breathing; Body position changes (sensors can be used to detect sudden changes in the user's body position). In case of an accident the body position can for example change from standing to prone. When the user is hurt he might remain in the prone position instead of recovering to a standing position.

For example, in a third situation 350 of example 300, the user 310 may remain in a lying position after falling. The user device 320 can determine that the measured vital parameter of the user deviates from the standard vital parameter of the user. For example, the user may breathe with a lower frequency after falling compared to before falling. The user device 320 may propose to the user to send an assistance requirement message. For example, if after a short time (e.g. less than 15 seconds, less than 10 seconds or less than five seconds) the gait and health parameters (or vital parameters) of the user do not return to normal (or the standard vital parameter), the device 200 may try to draw the user's attention and propose to warn the emergency services or a preset "in case of emergency" contact. The user device 200 may for example provide a button on a touchscreen of the user device 200 to the user and the user 310 could press the button for sending an assistance requirement message 352. For example, the user device 200 may provide an additional, second button to the user and the user may press the second button to stop the device automatically sending an assistance requirement message. If the user does not dismiss the proposal to warn emergency services, the user device 200 (for example a mobile phone) may proceed to send the assistance requirement message automatically to warn a preset "in case of emergency" contact.

According to a fourth situation 360 of example 300, the user 310 gets up again after falling and continues walking with the standard gait or the gait of the user before falling. The user device 320 still may initiate a measurement of the vital parameter or measure the vital parameter.

For example, in a fifth situation 370 (following the fourth situation 360) of example 300 the measured vital parameters of the user do not deviate from the standard vital parameters of the user after the user 310 has continued walking. For example, if the measured vital parameters of the user stay within the range of the standard vital parameters for more than two minutes (or more than five minutes or more than 10 minutes), the user device 320 may stop measuring the vital parameters. For example, the user device 320 may change back to an operation mode of waiting for detecting another acceleration measurement above the predefined acceleration threshold.

By contrast, according to a sixth situation 380 (following the fourth situation 360) of example 300, although the user 310 has continued walking after falling, the measured vital parameters of the user differ from the standard vital parameter. For example, the blood pressure of the user 310 may be lower than usual. It may be possible that the user 310 cannot perceive his vital state properly or classify it correctly, possibly caused by a state of shock he is in after falling. The user device 320 may for example provide an information 382 about the vital state of the user 310 to the user 310. The information 382 may comprise the vital parameter and may propose to the user to have a rest or to take some time for regenerating if the vital parameter deviates slightly from the standard vital parameter. The content of the information may depend on the degree of deviation of the vital parameter from the standard vital parameter of the user.

Some embodiments relate to collision accident detection for pedestrians. Embodiments of the disclosure relate to situations when a person has an accident (e.g. when the person is hit by a car or falls, etc.). An electronic device may detect the situation based on a combination of different user-based parameters (accelerometer, gait, heartbeat, blood pressure, skin response, etc.) and may automatically warn emergency services with a minimum of false positives. The electronic device may be a smartphone or wearable device like a smartwatch, heartbeat sensor, etc. Proposed concepts may limit the number of false positives by using different physical parameters of the user to determine if the user is actually in distress. For example, using concepts of the disclosure can help to get appropriate assistance to a pedestrian in distress. For example, assistance may be provided at, or in case of hit-and-run accidents without any helpful bystanders nearby.

Some embodiments relate to a software that may be used for detecting an emergency or distress situation. The software may be running locally on a user device or as a cloud service. The software may use accelerometers, gait, heartbeat, blood pressure, galvanic skin response, blood oxygen level, body position, body temperature, electromyography as inputs to determine the state of e.g. the pedestrian.

Measuring the vital parameters to check the condition of the user can be triggered by a high energy acceleration, and the method may be used to detect e.g. accidents in different scenarios: for supporting people falling from stairs or mountains; or for supporting cyclists falling due to getting hit by a car or hitting an obstacle in the road. Emergency services and "in case of emergency" contacts may be warned as soon as possible after an accident happened. This may increase the chance of help arriving in time to decrease the resulting injuries and future health impact in some cases.

A device may be implemented according to proposed concepts, e.g. if the device responds to sudden impacts to trigger scenarios to warn the emergency services or "in case of emergency" contacts and/or if the device connects to wearable health sensors to aggregate information to build a picture of the user's health.

A device according to the disclosure could be any of a Smartphone, a smartwatch, an electronic bracelet, and/or clothing with integrated electronics.

Aspects of the present disclosure are provided by the following examples.

Example 1 comprises a method for supporting a user, comprising providing an acceleration measurement of the user; measuring at least one vital parameter of the user if the acceleration measurement is above a predefined acceleration threshold; and signaling a need of assistance for the user if the measured vital parameter of the user deviates from a standard vital parameter of the user by more than a predefined threshold.

Example 2 comprises the method according to example 1, wherein the need for assistance is signaled depending on a degree of deviation between the measured vital parameter and the standard vital parameter.

Example 3 comprises the method according to example 1 or 2, wherein the measurement of the vital parameter comprises measuring at least one of a heartbeat of the user, blood pressure of the user, skin response of the user, blood oxygen level of the user and skin temperature of the user, wherein a wearable device of the user is used for measuring the vital parameter.

Example 4 comprises the method according to one of examples 1 to 3, wherein the wearable device is at least one of a smartwatch, a heartbeat sensor, a smart bracelet, and a smart garment.

Example 5 comprises the method according to one of examples 1 to 4, wherein in addition to measuring the vital parameter a position of the user is determined and signaling the need of assistance depends on the determined position of the user.

Example 6 comprises the method according to one of examples 1 to 5, wherein a gait of the user is determined by an electrical device of the user as the vital parameter.

Example 7 comprises the method according to one of examples 1 to 6, wherein the standard vital parameter of the user is an averaged vital parameter of a plurality of vital parameters of the user measured within a predefined time range before the acceleration measurement above the predefined acceleration threshold was detected.

Example 8 comprises the method according to one of examples 1 to 7, wherein the standard vital parameter of the user is determined based on a user profile determined during normal use of an electrical device used by the user.

Example 9 comprises the method according to one of examples 1 to 8, wherein the standard vital parameter of the user is an averaged vital parameter of the user based on a plurality of vital parameters of the user determined before the acceleration measurement above the predefined acceleration threshold was detected.

Example 10 comprises the method according to one of examples 1 to 9, wherein at least one measured vital parameter is transmitted to a cloud service and the standard vital parameter of the user is determined by the cloud service based on the at least one measured vital parameter.

Example 11 comprises the method according to one of examples 1 to 10, wherein signaling the need for assistance comprises proposing to the user, by an electrical device of the user, to let the electrical device send an assistance requirement message, wherein in the absence of a user reaction the assistance requirement message is sent automatically by the electrical device with a predefined time lag after the proposal.

Example 12 comprises the method according to example 11, wherein the assistance requirement message is sent to an emergency service if the deviation between the measured vital parameter and the standard vital parameter is more than 100%.

Example 13 comprises the method according to example 11 or 12, wherein the assistance requirement message comprises a location of the user or a location of the electrical device.

Example 14 comprises the method according to one of examples 1 to 13, wherein the predefined acceleration threshold used to initiate measuring the vital parameter is adjusted by the user.

Example 15 comprises a user device, comprising circuitry configured to provide an acceleration measurement of the user; configured to initiate a measurement of at least one vital parameter of the user if the acceleration measurement is above a predefined acceleration threshold; and configured to signal a need of assistance for the user, if the measured vital parameter of the user deviates from a standard vital parameter of the user by more than a predefined threshold.

Example 16 comprises the user device according to example 15, wherein the user device is configured to adjust the predefined acceleration threshold according to a setting of a user.

Example 17 comprises the user device according to example 15 or 16, further comprising a receiver configured to receive information about the vital parameter measured and transmitted by a wearable device of the user connected to the user device.

Example 18 comprises the user device according to one of examples 15 to 17, wherein the user device is configured to output at least one of an acoustic signal and a light signal to signal the need of assistance for the user.

Example 19 comprises the user device according to one of examples 15 to 18, further comprising a transmitter configured to send an assistance requirement message.

Example 20 comprises a computer program including program code, when executed, to cause a programmable processor to perform the method of one of examples 1 to 14.

Example 21 comprises a non-transitory machine readable storage medium including program code, when executed, to cause a programmable processor to perform the method of one of examples 1 to 14.

The aspects and features mentioned and described together with one or more of the previously detailed examples and figures, may as well be combined with one or more of the other examples in order to replace a like feature of the other example or in order to additionally introduce the feature to the other example.

Examples may further be or relate to a computer program having a program code for performing one or more of the above methods, when the computer program is executed on a computer or processor. Steps, operations or processes of various above-described methods may be performed by programmed computers or processors. Examples may also cover program storage devices such as digital data storage media, which are machine, processor or computer readable and encode machine-executable, processor-executable or computer-executable programs of instructions. The instructions perform or cause performing some or all of the acts of the above-described methods. The program storage devices may comprise or be, for instance, digital memories, magnetic storage media such as magnetic disks and magnetic tapes, hard drives, or optically readable digital data storage media. Further examples may also cover computers, processors or control units programmed to perform the acts of the above-described methods or (field) programmable logic arrays ((F)PLAs) or (field) programmable gate arrays ((F) PGAs), programmed to perform the acts of the above-described methods.

The description and drawings merely illustrate the principles of the disclosure. Furthermore, all examples recited herein are principally intended expressly to be only for illustrative purposes to aid the reader in understanding the principles of the disclosure and the concepts contributed by the inventor(s) to furthering the art. All statements herein reciting principles, aspects, and examples of the disclosure, as well as specific examples thereof, are intended to encompass equivalents thereof.

A functional block denoted as "means for . . ." performing a certain function may refer to a circuit that is configured to perform a certain function. Hence, a "means for s.th." may be implemented as a "means configured to or suited for s.th.", such as a device or a circuit configured to or suited for the respective task.

Functions of various elements shown in the figures, including any functional blocks labeled as "means", "means for providing a signal", "means for generating a signal.", etc., may be implemented in the form of dedicated hardware, such as "a signal provider", "a signal processing unit", "a processor", "a controller", etc. as well as hardware capable of executing software in association with appropriate software. When provided by a processor, the functions may be provided by a single dedicated processor, by a single shared processor, or by a plurality of individual processors, some of which or all of which may be shared. However, the term "processor" or "controller" is by far not limited to hardware exclusively capable of executing software, but may include digital signal processor (DSP) hardware, network processor, application specific integrated circuit (ASIC), field programmable gate array (FPGA), read only memory (ROM) for storing software, random access memory (RAM), and non-volatile storage. Other hardware, conventional and/or custom, may also be included.

A block diagram may, for instance, illustrate a high-level circuit diagram implementing the principles of the disclosure. Similarly, a flow chart, a flow diagram, a state transition diagram, a pseudo code, and the like may represent various processes, operations or steps, which may, for instance, be substantially represented in computer readable medium and so executed by a computer or processor, whether or not such computer or processor is explicitly shown. Methods disclosed in the specification or in the claims may be implemented by a device having means for performing each of the respective acts of these methods.

It is to be understood that the disclosure of multiple acts, processes, operations, steps or functions disclosed in the specification or claims may not be construed as to be within the specific order, unless explicitly or implicitly stated otherwise, for instance for technical reasons. Therefore, the disclosure of multiple acts or functions will not limit these to a particular order unless such acts or functions are not interchangeable for technical reasons. Furthermore, in some examples a single act, function, process, operation or step may include or may be broken into multiple sub-acts, -functions, -processes, -operations or -steps, respectively. Such sub acts may be included and part of the disclosure of this single act unless explicitly excluded.

Furthermore, the following claims are hereby incorporated into the detailed description, where each claim may stand on its own as a separate example. While each claim may stand on its own as a separate example, it is to be noted that—although a dependent claim may refer in the claims to a specific combination with one or more other claims—other examples may also include a combination of the dependent claim with the subject matter of each other dependent or independent claim. Such combinations are explicitly proposed herein unless it is stated that a specific combination is not intended. Furthermore, it is intended to include also features of a claim to any other independent claim even if this claim is not directly made dependent to the independent claim.

What is claimed is:

1. A method for supporting a user, the method comprising:
providing an acceleration measurement of the user;
measuring at least one vital parameter of the user if the acceleration measurement is above a predefined acceleration threshold; and
signaling a need of assistance for the user if the measured vital parameter of the user deviates from a standard vital parameter of the user,
wherein the standard vital parameter of the user is an averaged vital parameter of a plurality of vital parameters of the user measured within a predefined time range before the acceleration measurement above the predefined acceleration threshold was detected.

2. The method according to claim 1, wherein the need of assistance is signaled if the measured vital parameter of the user deviates from the standard vital parameter of the user by more than a predefined threshold.

3. The method according to claim 1, wherein the need of assistance is signaled depending on a degree of deviation between the measured vital parameter and the standard vital parameter.

4. The method according to claim 1, wherein the measurement of the vital parameter comprises measuring at least one of a heartbeat of the user, blood pressure of the user, skin response of the user, blood oxygen level of the user and skin temperature of the user, wherein a wearable device of the user is used for measuring the vital parameter.

5. The method according to claim 4, wherein the wearable device is at least one of a smartwatch, a heartbeat sensor, a smart bracelet, and a smart garment.

6. The method according to claim 1, wherein in addition to measuring the vital parameter a body position of the user is determined and signaling the need of assistance depends on the determined position of the user.

7. The method according to claim 1, wherein a gait of the user is determined by an electrical device of the user as the vital parameter.

8. The method according to claim 1, wherein at least one measured vital parameter is transmitted to a cloud service and the standard vital parameter of the user is determined by the cloud service based on the at least one measured vital parameter.

9. The method according to claim 1, wherein signaling the need for assistance comprises proposing to the user, by an electrical device of the user, to let the electrical device send an assistance requirement message, wherein in the absence of a user reaction the assistance requirement message is sent automatically by the electrical device with a predefined time lag after the proposal.

10. The method according to claim 9, wherein the assistance requirement message is sent to an emergency service if the deviation between the measured vital parameter and the standard vital parameter is over a predefined threshold.

11. The method according to claim 9, wherein the assistance requirement message comprises a location of the user or a location of the electrical device.

12. The method according to claim 1, wherein the predefined acceleration threshold used to initiate measuring the vital parameter is adjusted by the user.

13. A user device, comprising
circuitry configured to
provide an acceleration measurement of a user;
initiate a measurement of at least one vital parameter of the user if the acceleration measurement is above a predefined acceleration threshold; and to
signal a need of assistance for the user, if the measured vital parameter of the user deviates from a standard vital parameter of the user by more than a predefined threshold,
wherein the standard vital parameter of the user is an averaged vital parameter of a plurality of vital parameters of the user measured within a predefined time range before the acceleration measurement above the predefined acceleration threshold was detected.

14. The user device according to claim 13, wherein the user device is configured to adjust the predefined acceleration threshold and/or the predefined threshold used for determining a deviation of the vital parameter from the standard vital parameter according to a setting of the user.

15. The user device according to claim 13, further comprising a receiver configured to receive information about the vital parameter measured and transmitted by a wearable device of the user connected to the user device.

16. The user device according to claim 13, wherein the user device is configured to output at least one of an acoustic signal and a light signal to signal the need of assistance for the user.

17. The user device according to claim 13, further comprising a transmitter configured to send an assistance requirement message.

* * * * *